US005858782A

United States Patent [19]
Long et al.

[11] Patent Number: 5,858,782
[45] Date of Patent: Jan. 12, 1999

[54] FUNCTIONAL HUMAN HEMATOPOIETIC CELLS

[75] Inventors: Michael W. Long, Northville; George G. Pipia, Ann Arbor, both of Mich.

[73] Assignee: Regents of the University of Michigan, Ann Arbor, Mich.

[21] Appl. No.: 557,991

[22] Filed: Nov. 13, 1995

[51] Int. Cl.$^6$ ....................................................... C12N 5/00
[52] U.S. Cl. ........................ 435/372; 435/375; 435/334; 435/355; 435/372; 435/7.1
[58] Field of Search ................................. 435/240.2, 375, 435/334, 355, 372, 382, 7.1

[56] References Cited

U.S. PATENT DOCUMENTS

| | | | |
|---|---|---|---|
| 4,965,204 | 10/1990 | Civin | 435/240.27 |
| 5,130,144 | 7/1992 | Civin | 424/577 |
| 5,486,359 | 1/1996 | Caplan et al. | 424/93.7 |

OTHER PUBLICATIONS

Craig et al., "Use of Lectins for Characterization and Purification of Human Bone Marrow Cells that Express CD34," *J Hematotherapy*, 1:55–64, 1992.

Morstyn et al., "Purification of Hemopoietic Progenitor Cells from Human Marrow Using a Fucose Binding Lectin and Cell Sorting," *Blood*, 56:798–805, 1980.

van der Valk et al., "Immunohistochemistry in Bone Marrow Diagnosis Value of a Panel of Monoclonal Antibodies on Routinely Processed Bone Marrow Biopsies," *Am J Surgical Pathology*, 13(2):97–106, 1989.

Pipiya, et al., "Functional Assessment of Hematopoietic Lectin Expression on CD34$^+$ Cells", *Blood*, vol. 84, No. 10 (Suppl. 1), p. 575A, (1994) Abstract No. 2284.

Pipiya, et al., "Functional Human Hematopoietic Cells Express Galactose–Binding Cell Surface Lectins", *Blood*, vol. 86, No. 10 (Suppl. 1), p. 307A, (1995) Abstract No. 1215.

International Search Report for PCT US 96/18170, Nov. 13, 1996.

*Primary Examiner*—Jasemine C. Chambers
*Assistant Examiner*—Karen M. Hauda
*Attorney, Agent, or Firm*—Arnold, White & Durkee

[57] ABSTRACT

The present invention provides compositions of purified cells that are selectively enriched for proliferating hematopoietic progenitor cells. These cells are both CD34 positive and express a galactose-binding surface structure. Methods for the purification and use of these cells, for example, in improving transplantations and reducing graft-versus-host disease also are provided.

24 Claims, 5 Drawing Sheets

FUNCTIONAL HUMAN HEMATOPOIETIC CELLS

BACKGROUND OF THE INVENTION

Extent of Relevant Hematopoietic Diseases, and Blood/Bone Marrow Transplantation. Currently, bone marrow, cytokine-mobilized peripheral blood, and cord blood are used as sources of hematopoietic cells for both autologous (same-individual) and allogeneic (histocompatibility-matched individuals) transplant. The availability of purified populations of functional hematopoietic cells is important to both types of procedure. The use of bone marrow transplantation in the United States has grown from a few individuals in the late 1960s, to over 10,000 per year in the United States, and over 6,000 in Europe.[20-22] Bone marrow transplantation is performed for a variety of reasons. Autologous transplants are used primarily as a salvage procedure in which blood or bone marrow is taken and stored prior to an intensification of radiation or chemotherapy. This procedure is rapidly becoming an important adjuvant for the treatment of breast cancer, and other solid tumors. Autologous transplants also are used to treat hematological disorders such as lymphomas, and leukemia, although differences exist in the primary indication for this treatment modality between the U.S. and Europe.[20] Likewise, allogeneic blood or bone marrow transplantation are used in the treatment of hematological malignancies, aplastic anemia, a number of congenital disorders, and immunodeficiency disorders.[21]

Although the success of blood and bone marrow transplantation is undisputed, many difficulties still exist with the procedure, and, unfortunately, a number of patients cannot have, or do not survive, the procedure. Three major risk factors affect the outcome of bone marrow transplantation: purging of contaminating cancer cells, Graft Versus Host Disease (GVHD), and donor availability. Each of these can be reduced by the use of the functionally defined population of cells described above. In the case of autologous transplant, one of the mechanisms of disease-relapse is that malignant cells are infused with the hematopoietic cells. Thus, transplant cell preparations must be manipulated (i.e., purged) to remove malignant cells. The most effective way to do this is to positively select only the (functional) hematopoietic cells, therefor discarding the negative (cancer) cells. The use of the isolated functional cells described above improves the selection of hematopoietic cells by a factor of 10, thus greatly improving selection against contaminating malignant cells. In allogeneic transplants a major problem is that the immune cells in the donor marrow (i.e., the graft) immunologically reject the recipient's (i.e., the host) tissues. Thus, it is important in allogeneic to give as few donor cells as possible in order to prevent GVHD. Again, the use of lectin-positive cells will allow a 10-fold reduction in the number of cells given. These cells also might improve donor availability as the reduction in GVHD incidence could allow the use of donors with minor histo-compatibility mismatches. Finally, the ability to purify functional hematopoietic cells will provide an excellent target cell population for gene therapy approaches to treating molecular diseases.

Hematopoiesis, the process by which mature blood cells are produced throughout the lifespan of the individual (producing on the order of $10^{11}$–$10^{12}$ blood cells per day) is tightly controlled. During blood cell development, cell:cell interactions, hematopoietic growth factors, and other microenvironmental molecules all function in cohort to regulate the production of distinct blood cell lineages within the bone marrow. Hematopoietic cells express a remarkable variety of cell-surface structures that mediate these interactions.[1] Among these cell surface antigens, CD34, a 105–120 kDa glycoprotein, is expressed on the surface of human hematopoietic cells, and thus serves as an antigenic marker for their isolation and characterization.[2-4] $CD34^+$ cell populations also contain cells capable of both short-term, and long-term in vivo hematopoietic reconstitution.[5] The purification of such subsets of human hematopoietic cells using CD34 and/or other surface-markers, therefore, is important for their utility in bone marrow transplantation, and for their usefulness in understanding human stem cell biology. The functional characterization of human hematopoietic cells is dependent on in vitro assays.[6] However, these assays show that not all $CD34^+$ cells are functional in vitro, as only 10–20% of $CD34^+$ cells proliferate to give rise to colonies, or clones of differentiated progeny.[7-9] Other antigenic markers are used in conjunction with CD34 to further isolate and/or characterize hematopoietic cells. For example, the expression of the HLA-DR histocompatibility antigen defines more mature hematopoietic progenitor cells, and its absence, more primitive cells; other antigens, such as CD 71, Thy-1 or CD 45Ra, also mark more primitive cells.[10-12] None of these antigens, however, are expressed solely on the functional subset of $CD34^+$ cells, i.e., the proliferating and, hence, clonigenic cells. Therefore, the identification of a cell surface structure which solely identifies proliferating $CD34^+$ cells would represent an effective means for the isolation of these cells for clinical or scientific purposes. We report that all proliferating $CD34^+$ cells are found within a distinct subpopulation that expresses galactose-specific cell-surface lectins.

SUMMARY OF THE INVENTION

The present invention involves a method for producing a population of functional hematopoietic progenitor cells enriched for proliferating cells. In one embodiment, the method comprises (a) obtaining a population of precursor cells; (b) selecting $CD34^+$ cells from said population of precursor cells; and (c) further selecting cells expressing a galactose-binding surface structure from said $CD34^+$ cells.

The present invention also involves a population of purified hematopoietic progenitor cells enriched for proliferating cells prepared by a method comprising (a) obtaining a population of precursor cells; (b) selecting $CD34^+$ cells from said population of precursor cells; and (c) further selecting cells expressing a galactose-binding surface structure from said $CD34^+$ cells.

The present invention also involves a method of transplanting hematopoietic progenitor cells comprising providing a composition of proliferating progenitor cells comprising the steps of (a) obtaining a population of precursor cells; (b) selecting $CD34^+$ cells from said population of precursor cells; (c) further selecting cells expressing a galactose-binding surface structure from said $CD34^+$ cells; and (d) administering said $CD34^+$/galactose-binding cells to a subject in an amount effective to establish a population of hematopoietic cells in said subject.

The present invention further involves a method of reducing the risk of graft versus host disease comprising providing a composition of proliferating progenitor cells comprising the steps of (a) obtaining a population of precursor cells; (b) selecting $CD34^+$ cells from said population of precursor cells; (c) further selecting cells expressing a galactose-binding surface structure from said $CD34^+$ cells; and (d) administering said $CD34^+$/galactose-binding cells to a subject in an amount effective to establish a population of hematopoietic cells in said subject, wherein the risk of GVHD is reduced due to the administration of fewer cells.

In yet another aspect, the present invention involves a purified composition of hematopoietic progenitor cells, said cells expressing (a) a galactose-specific cell surface lectin; and (b) a CD34 glycoprotein.

BRIEF DESCRIPTION OF THE DRAWINGS

The following drawings are provided to aid in a better understanding of the present invention:

FIG. 1A: NALD cell binding to BSA-FITC. FIG. 1B: $CD34^+$ cell binding to BSA-FITC. FIG. 1C: $CD34^+$ cell binding to Gal-BSA-FITC.

FIG. 2A: Binding to Gal-NH-BSA, Gal-Nac-BSA and Lac-BSA. FIG. 2B: Binding to Gal-NH-BSA, Gal-NH-BSA in the presence of galactose and Gal-NH-BSA preceded by incubation with Gal-NH-BSA. FIG. 2C: Proliferation of $Lectin^+$ and $Lectin^-$ cells.

DETAILED DESCRIPTION OF THE INVENTION

Figures 1A, 1B, 1C:
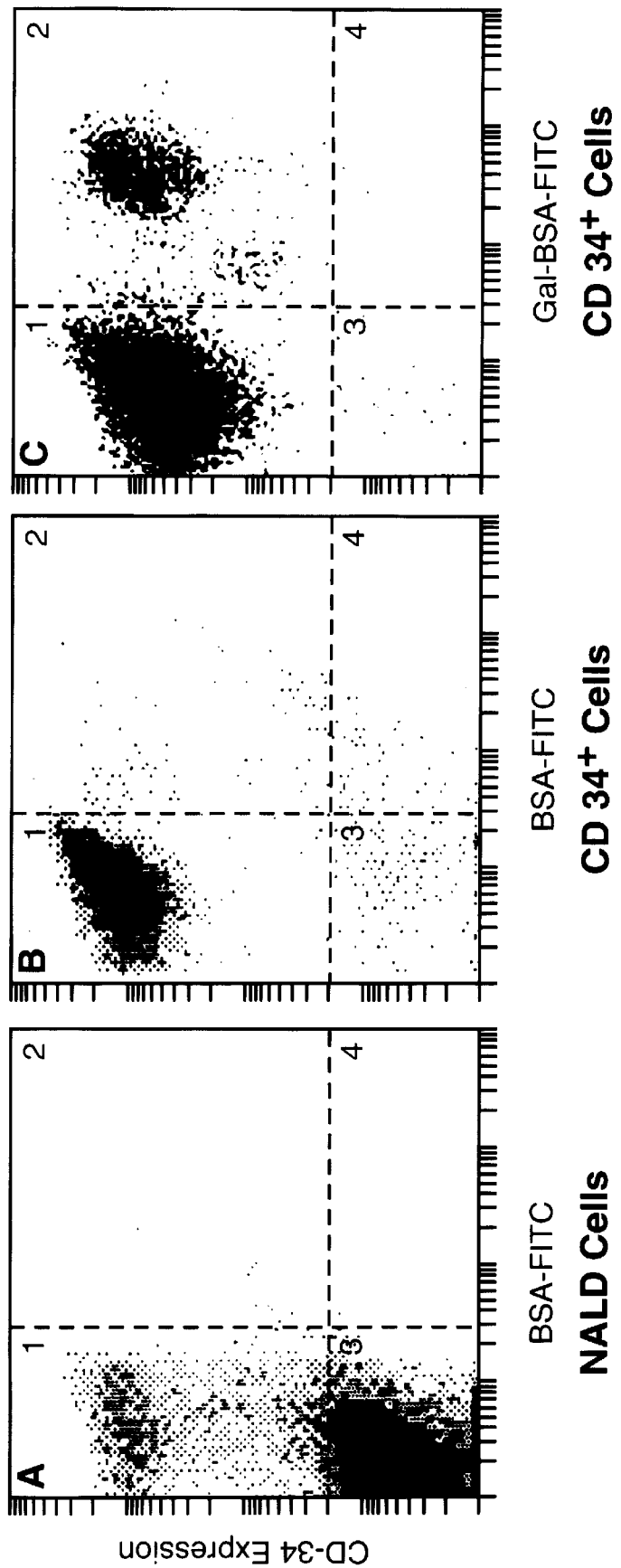
FIGS. 1A–1C—Flow Cytometric Analyses of Cell Binding.

In order to characterize hematopoietic cell-surface lectins, human $CD34^+$ cells were isolated from bone marrow non-adherent, low-density (NALID) cells by immuno-magnetic separation,(13,14) The capacity of $CD34^+$ cells to bind sugar residues was then determined by incubating $CD34^+$ cells with fluorescein isothiocyanate (FITC)-conjugated neoglycoproteins (i.e., BSA conjugated with specific mono- and disaccharide residues), using BSA-FITC as a control. Two-color flow cytometric analyses (15) demonstrate that neither NALD cells nor $CD34^+$ cells bind BSA-FITC to any significant degree (FIG. 1 A and B). In contrast, a subpopulation of $CD34^+$ cells (8.4±2.3 percent;x±SEM; n=7) specifically binds galactosyl-BSA (Gal-BSA) yielding a fluorescent signal 1–2 logs higher than background BSA-FTTC binding (FIG. 1C). The specificity of this binding was demonstrated by its inhibition by soluble galactose (0.25M), or preincubation of $CD34^+$ cells with un conjugated Gal-BSA (data not shown; vide infra).

Figures 2A, 2B, 2C:
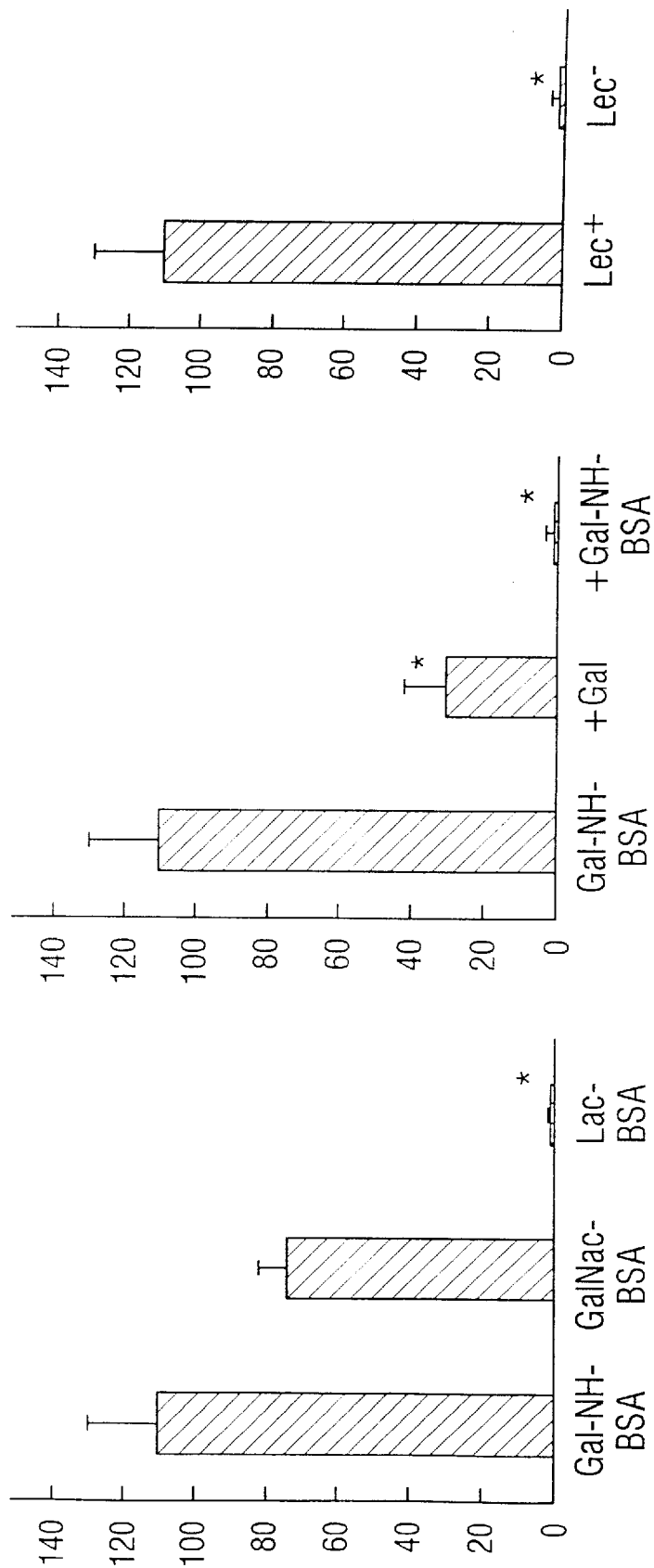
FIGS. 2A–C—Cell Adhesion and Proliferation Assays.
Figure 3A:
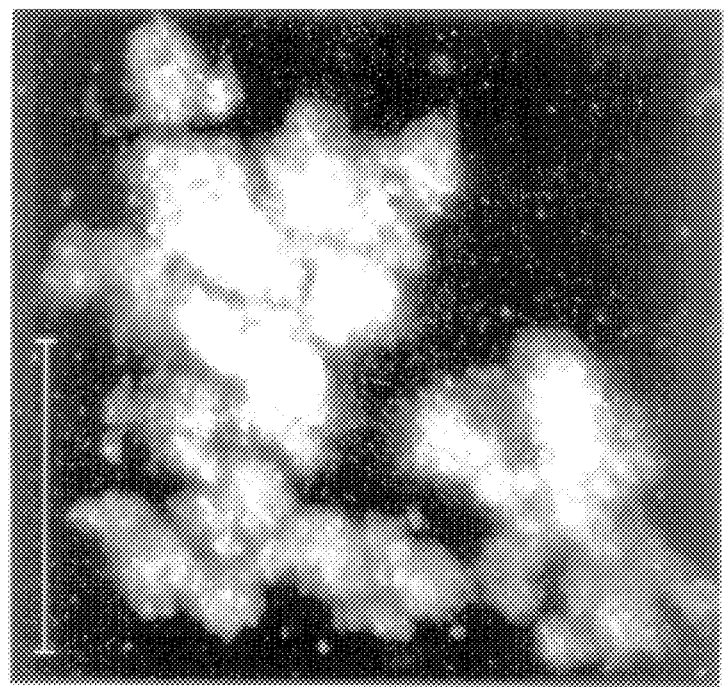
FIG. 3A—Photomicrograph of large, multifocol, multi-lineage cells from $CD34^{\pm}/Lectin^{35}$ Cells.
Figures 3B, 3C:
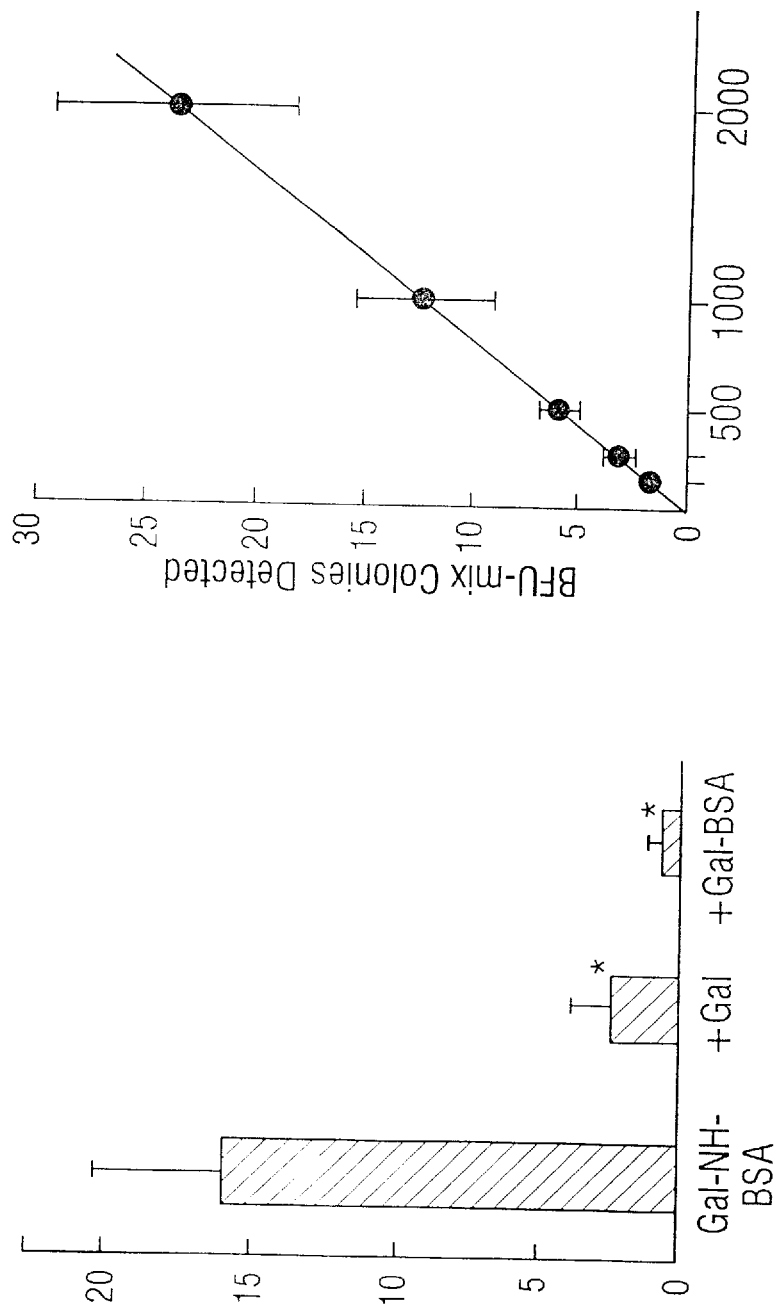
FIG. 3B—Attachment of BFU-mix Cells to Gal-NH-BSA. Specificity of BFU-mix binding to Gal-NH-BSA is shown by competition with Gal-NH and Gal-NH-BSA.
FIG. 3C—Linearity Study of Gal-NH-BSA-Adherent $CD34^{\pm}$ Cells.

We reasoned that if galactose-binding was functionally significant, then Gal-BSA might serve as a ligand for $CD34^+$ cells in cytoadhesion assays.(16) Gal-BSA and other neoglycoproteins were immobilized onto tissue culture plastic, as described previously for other proteins (17), and used as target adhesion molecules for $CD34^+$ cells. Preliminary studies, using fluorescently-tagged $CD34^+$ cells indicated that equivalent numbers of cells could be isolated by neoglycoprotein-binding as were seen in the flow cytopmetry studies. Importantly, studies of hematopoietic progenitor cells indicate that the same number of $CD34^+$ colony-forming hematopoietic cells adhere to immobilized Gal-BSA, ord to galactosamide-BSA (Gal-NH-BSA; FIG. 2A), and that this number was equivalent to the input number of progenitor cells. These lectin-positive cells thus contained all the proliferating progenitor cells of each myeloid lineage: granulocytic, erythrocytic, and megakaryocytic. Modification of the galactosyl-residue to N-acetyl-galactosaminide-BSA (GalNac-BSA), however, resulted in a slight, but insignificant ($p \geq 0.5$), reduction in attachment, whereas BSA conjugated to lactose failed to bind hematopoietic progenitor cells. The specificity of Gal-BSA attachment was again confirmed by the inhibition of hematopoietic progenitor cell attachment by soluble sugar (0.25M galactose), or pre-incubation with Gal-NH-BSA (FIG. 2B). The attachment of $CD34^+$ hematopoietic progenitor cells to Gal-NH-BSA suggested that all of the functional $CD34^+$ cells expressed a galactose-binding lectin on their surface. However, the formal possibility remained that galactose-binding stimulated self-renewal of the neoglycoprotein-adherent progenitor sells, thus increasing the number of galactose-bound cells. This possibility was excluded in another series of experiments in which both the Lectin-positive, and Lectin-negative $CD34^+$ cells were examined for the presence of hematopoietic progenitor cells. In these studies, the $CD34^{+,}$ $_{Lectin}{}^-$ cells repeatedly failed to form hematopoietic colonies, while the $CD34^+$, $Lectin^+$ cells consistently contained 100% of the proliferating progenitor cells (FIG. 2C). We next evaluated the $CD34^+$, $Lectin^+$ cell population for the presence of long-term culture initiating cells (LTC-IC), a population of cells capable of initiating and maintaining long-term hematopoiesis in vitro.(18) Our studies indicate that ≈75% of the LTC-IC were within the $CD34^+$, $Lectin^+$ subpopulation (data not shown). Thus, all of the functional hematopoietic progenitor cells are found within the $CD34^+$, $Lectin^+$ cell population Interestingly, a new human hematopoietic progenitor cell phenotype is observed among the $CD34^+$ $Lectin^+$ cells that is not observed among cells isolated by $CD34^+$ expression alone. This high-proliferative potential progenitor cell gives rise to large, multi-focal, multi-lineage colonies (FIG. 3A). The proliferative potential of these progenitor cells is indicated by both their cellularity (as indexed by a colony size of 0.5–2.0 mm in diameter), and their multi-focal (or burst-like) appearance. The multi-lineage potential of these cells is shown by both their colony-morphology (i.e. colonies contain both hemoglobinized and non-hemoglobinized cells) and their cellular composition. Cytocentrifuge preparations (19) of individual "burst-colonies" showed mixed cellularity, containing 3–4 blood cell lineages: granulocytes/macrophages, normoblasts, megakaryocytcs, and lymphoid cells. In contrast, the morphology of erytliroid burst-forming colonies (BFU-e) showed only hemoglobinized cells, and cytocentrifuge preparations coniirmed their uni-lineage nature (data not shown). Gives their burst-like appearance and mixed cellularity, we refer to these new $CD34^+$, $Lectin^+$ progenitor cells as burst-forming units (cells) of mixed-cellularity (BFU-mix). As with other $CD34^+$ progenitor cells, the specificity of attachment of the BFU-mix to Gal-NH-BSA is demonstrated by binding-inhibition using 0.25M galactose, or Gal-NH-BSA (FIG. 3B). Finally, the single-cell origin of these colonies was shown in a linearity study (FIG. 3C) in which limiting cell dilutions (down to 250 $CD34^+$, $Lectin^+$ cells/mL) of Gal-NH-BSA-adherent $CD34^+$ cells were shown to have a linear relationship to the number of BFU-mix colonies detected, (with the x-y intercept occurring at zero). In order to investigate their self-renewal potential, individual BFU-mix colonies were examined for their replating potential. Individual BFU-mix were picked from the methylcellulose cultures, mono-dispersed, and replated into secondary cultures.(20) Approximately 10–20% of the BFU-mix generate high-proliferative potential colony forming cells (HPP-CFC) in secondary cultures, but did not generate secondary BFU-mix, nor tertiary colonies of any type (Table 1). BFU-e, picked and replated as controls, failed to generate any colonies in secondary cultures.

The generation of HPP-CFC from BFU-mix in secondary cultures demonstrates that the BFU-mix are developmentally antecedent to the HPP-CFC, but are not capable of self-renewal on vitro. The possibility that BFU-mix are erythroid burst-forming cells (BFU-e) was excluded by a number of criteria: (1) both colonies have distinctly differing phenotypes (Re. FIG. 1A), (2) both colonies co-exist in the same cultures, thus excluding a bias in culture growth conditions, (3) 100% of the BFU-e are recovered on immobilized Gal-NH-BSA, thus excluding a developmental relationship in which BFU-miix give rise to BFU-e, (4) cytocentrifuge preparations of BFU-e confirm their uni-lineage erythroid nature where as BFU-mix are muti-lineage, and (5) BFU-mix, but not BFU-e, have secondary replating potential. Based on their high proliferative potential, BFU-mix are developmentally simnilar to other primitive hematopoietic cells such as the burst-forming megakaryocyte progenitor cells, (BFU-Mk), the high-proliferative potential colony forming cell (HPP-CFC), or subsets of erythroid burst-forming cells seen in human cord blood.(17,21,22) However, HPP-CFC are distinctly different from BFU-mix in HPP-CFC lack the capacity to generate cells of the erythroid lineage, and have a distinctly different colony morphology.(21)

Figure 4:
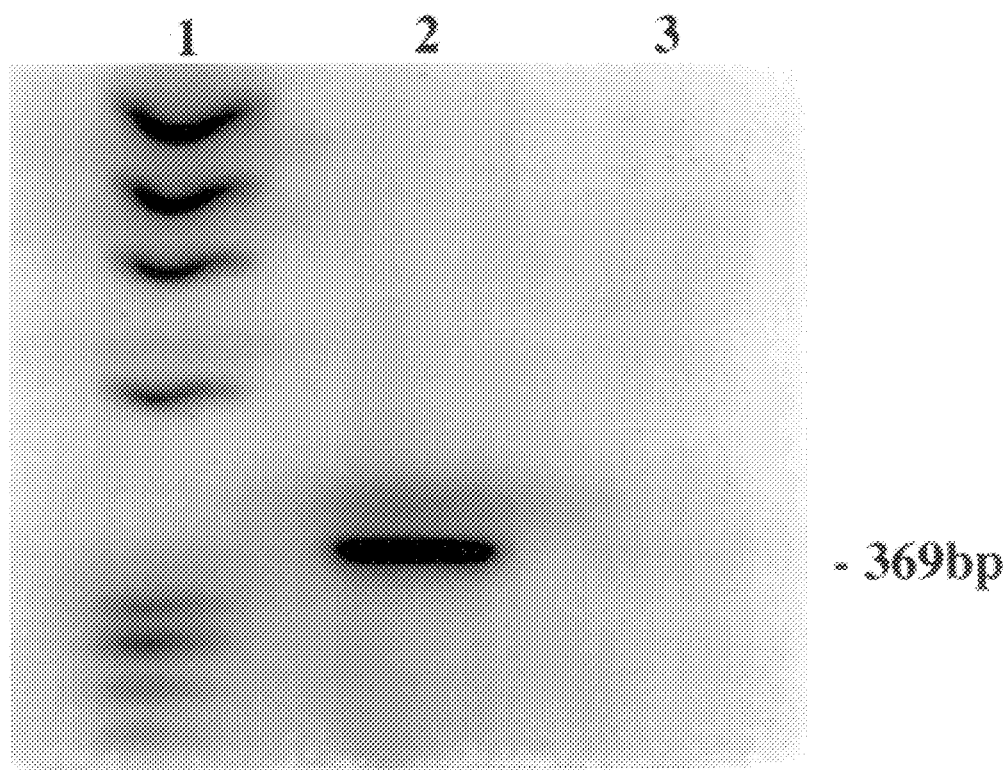
FIG. 4—Amplification of Galectin cDNA. Primer amplification of a 369 bp product from cDNA of galectin-positive cells. This product is missing from cDNA of $CD34^+$ cells.

Recently, a gene-family of lectins with galactose-binding specificity (galectins) was described.(23) While most members of this family are either soluble, or intracellular lectins, we nonetheless evaluated CD34$^+$ cells for galectin gene expression by RT-PCR.(24) These studies employed deoxynucleotide primers designed to both amplify the conserved carbohydrate-recognition domain (CRD) found within the carboxy terminus of these lectins.(25) These primers detected the predicted 369 bp product in the control (galectin-positive) ZR-75-1 cells, but failed to amplify cDNA from CD34$^+$ cells (FIG. 4), We conclude that all proliferating, or functional CD34$^+$ cells are found among a subpopulation that expresses a galactose-specific lectin. Thus, CD34$^+$, Lectin$^+$ positive cells contain both primitive hematopoietic cells with stein cell-like characteristics (LTC-IC, BFU-mix, HPP-CFC, and BFU-Mk), as well as more mature progenitive cells (BFU-e, CFU-gemm, CFU-Mk, and CFU-GM). Furthermore, these data on human CD34$^+$ Lectin$^+$ cells are consistent with murine studies in which long-term hematopoietic cell engraftment was partially blocked by galactose-containing neoglycoproteins.(26) The use of galactose-specific lectin expression in conjunction with CD34 results in a rapid, two-step purification of functional, proliferating human hematopoietic cells. Importantly, progenitor cells of all lineages, and each of the four known primitive, high-proliferative potential human hematopoietic progenitor cells (LTC-IC, BFU-mix, HPP-CFC, and BFU-Mk) are found in this purified cell population, strongly suggesting that both short-term and long-term repopulating cells are among the CD34$^+$, Lectin$^+$ cell population. Thus, the use of the CD34$^+$ Lectin cells should be helpful in both bone-marrow, or peripheral blood hematopoietic cell transplantation. Moreover, the evaluation of CD34$^+$, Lectin$^+$ cells also should provide important information regarding hematopoietic cell function in health and disease.

This invention consists of a cellular product of isolated, purified human hematopoietic cells, and the means to isolate and purify these cells for scientific or clinical use. Thus, a patient's own blood or bone marrow precursor cells, or those of a histo-compatible donor, can be removed, purified, and used for autologous or allogeneic transplantation. Autologous or allogeneic transplantation are of therapeutic importance in the treatment of many blood cell disorders, and are important as an adjuvant in cancer therapy. Purified human hematopoietic cells are also an ideal target for human gene therapy for disorders in which a known, specific molecular defect results in abnormal function. The ability to isolate and purify functional populations cells demonstrates that they can be used as target cells for gene therapy of congenital defects. Another advantage in using this functional population of hematopoietic cells is that they are more highly purified than other cell preparations. As a result fewer cells are administered during the transplantation process. This markedly reduces the antigenic burden in the situation of allogeneic transplants (see below).

Alternative Methods of Obtaining the Invention. This population of cells can be obtained by subjecting CD34$^+$ hematopoietic cells to a variety of cytoadhesion-based procedures. These are comprised of, but not limited to, fluorescence-activated flow cytometry, immunological or glycoconjugate-based column chromatography, conjugated sepharose beads (or other inert beads), or other glycoconjugate-based applications. These procedures both define the population of human hematopoietic cells, and lead to its isolation. Other physical separation procedures may be applied prior or after the Lectin-1 purification. These are comprised of, but not limited to, equilibrium density centrifugation, velocity sedimentation, or counter-flow centrifugal elutriation. As well, other antigenic markers may be used to positively or negatively further define these cells. These are composed of, but not limited to, antigens of the human major histocompatibility locus (particularly HLA-DR), hematopoietic antigens (e.g., CD33, CD8, CD10, CD14, CD9, CD20), or other surface proteins, such as Thy 1. These human hematopoietic cells described herein are isolated from human bone marrow. Sources of such marrow are the flat bones of the axial skeleton (ribs, hips, sternum), as well as the humeri, radi, ulna, tibiae, and fibulae. Additionally, these cells also can be obtained from cord blood, peripheral blood, or cytokine-mobilized peripheral blood.

What is claimed is:

1. A method of producing a purified population of CD34$^+$, galactose-specific lectin$^+$, proliferating human hematopoietic progenitor cells comprising the steps of:
    (a) obtaining a population of human hematopoietic progenitor cells;
    (b) selecting CD34$^+$ cells from said population of human hematopoietic progenitor cells; and
    (c) selecting a galactose-specific lectin on said CD34$^+$ cells; wherein a purified population of CD34$^+$, galactose-specific lectin$^+$ proliferating hematopoietic progenitor cells are obtained.

2. The method of claim 1, wherein said purified population of human hematopoietic progenitor cells contain long-term culture initiating cells (LTC-IC), burst-forming unit mix (BFU-mix), burst-forming unit megakaryocyte cells (BFU-Mk), high proliferative potential-colony-forming cells (HPP-CFC), colony-forming unit granulocyte macrophages (CFU-GM), colony-forming unit granulocyte erythrocyte macrophage megakaryocytes (CFU-gemm), burst-forming unit erythrocytes (BFU-E) or colony-forming unit megakaryocytes (CFU-Mk).

3. The method of claim 1, wherein hematopoietic progenitor cells of step (a) are obtained from human bone marrow, cord blood, peripheral blood or cytokine mobilized peripheral blood.

4. The method of claim 1, wherein said CD34$^+$ cells are immunologically selected using an antibody immunoreactive with the cell surface antigen CD34.

5. The method of claim 1, wherein said purified population of proliferating CD34$^+$, galactose-specific lectin$^+$ hematopoietic progenitor cells are selected using cytoadhesion.

6. The method of claim 4, wherein said immunologic selection is by immunomagnetic separation.

7. The method of claim 5 wherein said cytoadhesion uses binding to galactose.

8. The method of claim 5 wherein said cytoadhesion uses binding to N-acetyl galactosamine.

9. The method of claim 8, wherein said N-acetyl galactosamine cytoadhesion is affinity chromatography.

10. The method of claim 9, wherein the N-acetyl galactosamine is conjugated to BSA.

11. The method of claim 1, wherein said the population of human hematopoietic progenitor cells of step (a) are purified by equilibrium density centrifugation prior to step (b).

12. The method of claim 1, wherein said purified population of proliferating CD34$^+$, galactose-specific lectin$^+$ hematopoietic progenitor cells are further fractionated according to size.

13. The method of claim 1, further comprising fractionating said purified population of proliferating CD34$^+$, galactose-specific lectin$^+$ hematopoietic progenitor cells by fluorescence activated flow cytometry, velocity sedimentation or counter flow centrifugal elutriation.

14. The method of claim 1, wherein the CD34$^+$ cells selected in step (b) are further selected for expression of HLA-DR, CD33, CD10, CD20 or Thy1.

15. The method of claim 1, wherein the CD34$^+$ cells selected in step (b) are further screened for cells that lack HLA-DR, CD33, CD8, CD10, CD 14, CD9, CD20 or Thy1.

16. A purified population of CD34$^+$, galactose-specific lectin$^+$ proliferating human hematopoietic progenitor cells prepared by the process of:
(a) obtaining a population of human hematopoietic progenitor cells;
(b) selecting CD34$^+$ cells from said population of human hematopoietic progenitor cells; and
(c) selecting a galactose-specific lectin on said CD34$^+$ cells; wherein a purified population of proliferating CD34$^+$, galactose-specific lectin$^+$ hematopoietic human progenitor cells are obtained.

17. The population of claim 16, wherein said purified population of CD34$^+$, galactose-specific lectin$^+$ hematopoietic progenitor cells are isolated using cytoadhesion.

18. The population of claim 17, wherein said cytoadhesion uses binding to galactose.

19. The population of claim 17, wherein said cytoadhesion uses binding to N-acetyl galactosamine.

20. The population of claim 16, wherein the population of human hematopoietic progenitor cells of step (a) are purified by equilibrium density centrifugation prior to step (b).

21. The population of claim 16, wherein said purified population of CD34$^+$, galactose-specific lectin$^+$ hematopoietic progenitor cells are further fractionated according to size.

22. The population of claim 16, wherein said purified population of CD34$^+$, galactose-specific lectin$^+$ hematopoietic progenitor cells are further fractionated by fluorescence activated flow cytometry, velocity sedimentation, or counter flow centrifugal elutriation.

23. The population of claim 16, wherein the CD34$^+$ cells selected in step (b) are further selected for expression of HLA-DR, CD33, CD10, CD20 or Thy1.

24. The population of claim 16, wherein the CD34$^+$ cells selected in step (b) are further screened for cells that lack HLA-DR, CD33, CD8, CD10, CD14, CD9, CD20 or Thy1.

* * * * *